: US 7,221,975 B2
(45) Date of Patent: May 22, 2007

(12) United States Patent
Lindström

(54) SIGNAL FILTERING USING ORTHOGONAL POLYNOMIALS AND REMOVAL OF EDGE EFFECTS

(75) Inventor: Lars Lindström, Molndal (SE)

(73) Assignee: Maquet Critical Care AB (SE)

( * ) Notice: Subject to any disclaimer, the term of this patent is extended or adjusted under 35 U.S.C. 154(b) by 369 days.

(21) Appl. No.: 10/728,081

(22) Filed: Dec. 4, 2003

(65) Prior Publication Data

US 2005/0125473 A1   Jun. 9, 2005

(51) Int. Cl.
 *A61B 5/04* (2006.01)
(52) U.S. Cl. ..................... 600/509; 128/901
(58) Field of Classification Search ............... 128/901; 600/509; 455/78; 324/76; 708/300, 313
See application file for complete search history.

(56) References Cited

U.S. PATENT DOCUMENTS

| 5,025,794 A | | 6/1991 | Albert et al. | |
| 5,318,036 A | * | 6/1994 | Arand et al. | 600/508 |
| 5,502,663 A | * | 3/1996 | Lyon | 708/300 |
| 5,579,243 A | * | 11/1996 | Levine | 708/300 |
| 5,603,321 A | * | 2/1997 | Kynor et al. | 600/409 |
| 6,988,116 B2 | * | 1/2006 | Corless et al. | 708/300 |

FOREIGN PATENT DOCUMENTS

WO   WO99/60701   11/1999

OTHER PUBLICATIONS

Falk, K.J. et al., "Real-Time Processing of Multiple-Lead Exercise Electrocardiograms," Medical Progress Through Technology, vol. 8, pp. 159-174, 1982.

Sinderby, C. et al., "Automatic Assessment of Electromyogram Quality," Journal of Applied Physiology, vol. 79, No. 5, pp. 1803-1815, 1995.
Taha, S.M.R. et al., "Computer-Aided Interpretation of ECG Signals Using Polynomial Regression Methods," Journal of Biomedical Engineering, vol. 11, pp. 329-333, Jul. 1989.
Moody, G.B. et al., "Derivation of Respiratory Signals from Multi-Lead ECGs," Institute of Electronics Engineers—Proceedings of the Computers in Cardiology Meeting, Linkoping, Sweeden, pp. 113-116, Sep. 1985.
Harris, F.J., "On the use of Windows for Harmonic Analysis with the Discrete Fourier Transform," Proceedings of the IEEE, IEEE, New York, vol. 66, No. 1, pp. 51-84, 1978.
Ambos, H.D. et al., "Spectral Analysis of the Entire Cardiac Cycle from Signal-Averaged ECGs for the Detection of Patients Prone to Ventricular Tachycardia," Computers in Cardiology, pp. 373-376, Sep. 1988.

* cited by examiner

*Primary Examiner*—Robert E. Pezzuto
*Assistant Examiner*—Brian T. Gedeon
(74) *Attorney, Agent, or Firm*—Kirkpatrick & Lockhart Preston Gates Ellis, LLP

(57) ABSTRACT

A method and device for filtering an input signal containing wanted signal components and unwanted signal components, wherein the signal is modeled as a set of polynomials. Polynomials from the set are identified to model the unwanted signal components. These unwanted signal components are removed from the input signal by removing the polynomials identified as modeling the unwanted signal components from the set of polynomials to thereby leave in the input signal only the wanted signal components. According to an alternative, polynomials from the set are identified to model the wanted signal components, and the polynomials identified as modeling the wanted signal components are outputted as an estimate of the wanted signal components substantially free from the unwanted signal components. According to another aspect, a weighting factor indicative of signal strength is determined for each polynomial and these weighting factors are summed to provide an estimate of the strength of the input signal.

77 Claims, 12 Drawing Sheets

SIGNAL FILTERING USING ORTHOGONAL POLYNOMIALS AND REMOVAL OF EDGE EFFECTS

FIELD OF THE INVENTION

The present invention relates to a method and device for filtering an input signal containing wanted signal components and unwanted signal components.

BACKGROUND OF THE INVENTION

Characteristics of typical signals, disturbances, noise and interference including myoelectric (EMG) signals, cardiac (ECG) signals, movement-induced disturbances, background noise, and interference from the mains will be first reviewed.

Myoelectric (EMG) Signal

An EMG signal reflects the nervous activation of a muscle or a group of muscles, and presents the character of a band-limited noise in extra-muscular readings. The strength and spectral contents of an EMG signal are determined by the following parameters:

(1) the number of motor units (muscles) recruited;
(2) the repetition rate of motor unit activation;
(3) the distance between the source (fibers of the muscle(s)) and the electrode(s) used to sense the EMG signal;
(4) the width of the innervation zone;
(5) the propagation velocity of the activation potentials;
(6) the electrode configuration including, for example, the distance between electrode plates, the parallel or perpendicular alignment of the electrode plates with respect to the direction of the fibers of the muscle(s), etc.; and
(7) other parameters such as the length of the fibers of the muscle(s), the position of the electrode(s) with respect to both the innervation zone and the ends of the fibers of the muscle(s), etc.

For many muscles, except very short muscles, the above-mentioned parameters produce a spectrum whose amplitude increases from zero at zero frequency (Direct Current (DC)), presents a peak in the region of 40–100 Hz and, then, decreases gradually as the frequency increases.

Models that take into consideration the above listed parameters show that these parameters are multiplicative in the frequency domain, indicating that the time dependent signals are multiple convolutions of the phenomena associated with these parameters. The time representation of an EMG signal is thus very complex, and most attempts to process such a signal has consequently involved filtering of the EMG signal through certain frequency-filtering characteristics.

Electrocardiogram (ECG) Signal

An ECG signal is generated from electrical activity of the heart, which is rather coherent in space and time. Thus, an ECG signal has a deterministic character in the time domain except under certain pathological conditions such as fibrillation. In the frequency domain, maximum density of the spectral energy is found in the region around 10–15 Hz with the spectral energy density decreasing as the frequency increases.

Since contributions to the ECG signal are synchronized, the ECG signal has a much higher energy than an EMG signal. Moreover, significant ECG contributions are located in the frequency bandwidth where the density of energy of an EMG signal is maximal, whereby ECG is likely to disturb an EMG signal.

Movement Induced Disturbance

Movement of the electrodes cause variations in the electrode contact resistance and electrode contact capacitance, which modulate the (half-battery) voltage across the metal-tissue junction to cause a corresponding disturbance. This disturbance, often referred to as "varying baseline", has high-amplitude low-frequency spectral components since it is caused by a slow mechanical movement. The frequency characteristic of this disturbance is often lower in frequency than the frequency characteristic associated with the time window of the signal epoch and, thus, this disturbance manifests itself as a large offset DC component.

It is also observed that variations in the baseline are equivalent to variations in the spectral components above DC (zero frequency). Therefore, the large potential behind baseline variations (magnitude of the order of, for example, one volt) also makes the spectrum density of the variation significant.

Background Noise

In addition to the above-mentioned signal contributions, there is a noise component. This noise component has a rather unspecific character and originates from a number of different sources. It is often modelled as a random component with constant (or slowly varying) spectral density in the whole frequency bandwidth of interest.

Interference from the Mains

Interference from the mains has a well-defined signal shape with a fixed frequency. Unknown parameters of this interference are the phase and the amplitude, which may vary considerably.

Currently Used Filter Techniques to Separate Signal Contributions

In the following description, some of the problems associated with the separation of signal components such as EMG, ECG, baseline variations, and noise will be discussed. Drawbacks associated with currently used signal filtering methods will also be considered.

EMG Signal vs. Movement Induced Disturbance

Although rather separated in frequency, the high energy density of the movement induced disturbances becomes significant also in the frequency bandwidth where EMG signals have a maximum amplitude. Recursive filtering is often used to remove movement induced disturbances from EMG signals. However, recursive filtering presents the drawback of suffering from the long time it takes to forget the high energy input from a sudden baseline variation. For that reason, recursive filtering should be avoided.

EMG Signal vs. Background Noise

The spectra of EMG signal and background noise overlap and both have a character of random noise. Optimum (Wiener) filtering can be used, but a low-pass filter cutting off the high frequency portion of the noise can be sufficient since this will remove the major portion of the background noise.

EMG Signal vs. ECG Signal

As indicated in the foregoing description, EMG and ECG signals have partly overlapping power spectra. Strong ECG signals create significant spectral energy density at frequencies where energy peaks of the EMG signals appear. Efficient filtering to remove an ECG signal from an EMG signal or vice versa should use the deterministic character of the ECG signal in the time domain.

ECG Signal vs. Movement Induced Disturbance

ECG signals and movement induced disturbances have respective spectra with a considerable overlap and are difficult to separate in the frequency domain. The deterministic character of ECG in the time domain is often utilized, in particular for averaging QRS complexes. A drawback of such filtering is that it introduces in the output from the filter a delay having a duration as long as ten (10) seconds.

ECG Signal vs. Background Noise

Although ECG signals and background noise overlap in the low frequency region of the spectrum, the ECG signal is mostly dominating and, therefore, a low-pass filtering is normally sufficient to remove most of the background noise from an ECG recording.

Movement Induced Disturbance vs. Background Noise

Although this case is of interest in quality control of the signal, this issue will not be further elaborated in the present specification.

Interference from the Mains and Power Line Interference

A common technique for removing an interference from the mains and a power line interference is to process the disturbed signal through a notch filter which is quite sharp at the particular frequency of these interferences. This solution presents the drawback that a notch filter introduces large phase shifts in the remaining part of the signal. As mentioned hereinabove, the nature of these interferences is "a priori" well known, and their frequency is mostly constant. Only the start instant within the oscillation, the phase, and the amplitude are unknown and have to be calculated. This "a priori" knowledge implies that single periods or even portions of the interference oscillation can be used to perform the latter calculation.

From the above-described characteristics of the various signal contributions, the following acknowledgments can be made:

Filtering in the frequency domain requires very steep filters to extract the EMG signal and to suppress the ECG signal and the interference from the mains. Steep filters present the drawback of being associated with large phase shifts and ringing.

Since the baseline variations are large and slow, recursive filtering should be avoided since these filters have a memory of past events.

Filtering should occur over finite epoch lengths, and Infinite Impulse Response (IIR) filters should not be used.

Filters designed from a frequency-domain point of view present the drawbacks of having 1) slow convergence since the trigonometric series are not well suited to describe baseline variations, 2) remaining memory of earlier events due to their (often) recursive character, and 3) large phase shifts and ringing in proportion of their sharpness.

In view of the above, a new filtering technique is needed to efficiently isolate or remove one or many of the above discussed signal contributions from an input signal.

SUMMARY OF THE INVENTION

More specifically, in accordance with the present invention, there is provided a method of filtering an input signal containing wanted signal components and unwanted signal components, comprising modeling the input signal as a set of polynomials, identifying polynomials from the set to model the unwanted signal components, and removing the unwanted signal components from the input signal by removing the polynomials identified as modeling the unwanted signal components from the set of polynomials to thereby leave in the input signal only the wanted signal components.

The present invention also relates to a device for filtering an input signal containing wanted signal components and unwanted signal components, comprising means for modeling the input signal as a set of polynomials, means for identifying polynomials from the set to model the unwanted signal components, and means for removing the unwanted signal components from the input signal, wherein the unwanted signal components removing means comprises means for removing the polynomials identified as modeling the unwanted signal components from the set of polynomials to thereby leave in the input signal only the wanted signal components.

Further in accordance with the present invention, there is provided a method of filtering an input signal containing wanted signal components and unwanted signal components, comprising modeling the input signal as a set of polynomials, identifying polynomials from the set to model the wanted signal components, and outputting the polynomials identified as modeling the wanted signal components as an estimate of the input signal substantially free from the unwanted signal components.

The present invention further relates to a device for filtering an input signal containing wanted signal components and unwanted signal components, comprising means for modeling the input signal as a set of polynomials, means for identifying polynomials from the set to model the wanted signal components, and means for outputting the polynomials identified as modeling the wanted signal components as an estimate of the input signal substantially free from the unwanted signal components.

Still further in accordance with the present invention, there is provided a method of filtering an input signal containing wanted signal components and unwanted signal components, comprising modeling the input signal as a set of polynomials, determining, for each polynomial, a weighting coefficient indicative of signal strength, and summing the weighting coefficients to provide an estimate of the strength of the wanted signal components.

The present invention still further relates to a device for filtering an input signal containing wanted signal components and unwanted signal components, comprising means for modeling the input signal as a set of polynomials, means for determining, for each polynomial, a weighting coefficient indicative of signal strength, and means for summing the weighting coefficients to provide an estimate of the strength of the wanted signal components.

The foregoing and other objects, advantages and features of the present invention will become more apparent upon reading of the following non-restrictive description of illustrative embodiments thereof, given by way of example only with reference to the accompanying drawings.

DETAILED DESCRIPTION OF THE ILLUSTRATIVE EMBODIMENT

Figure 1:
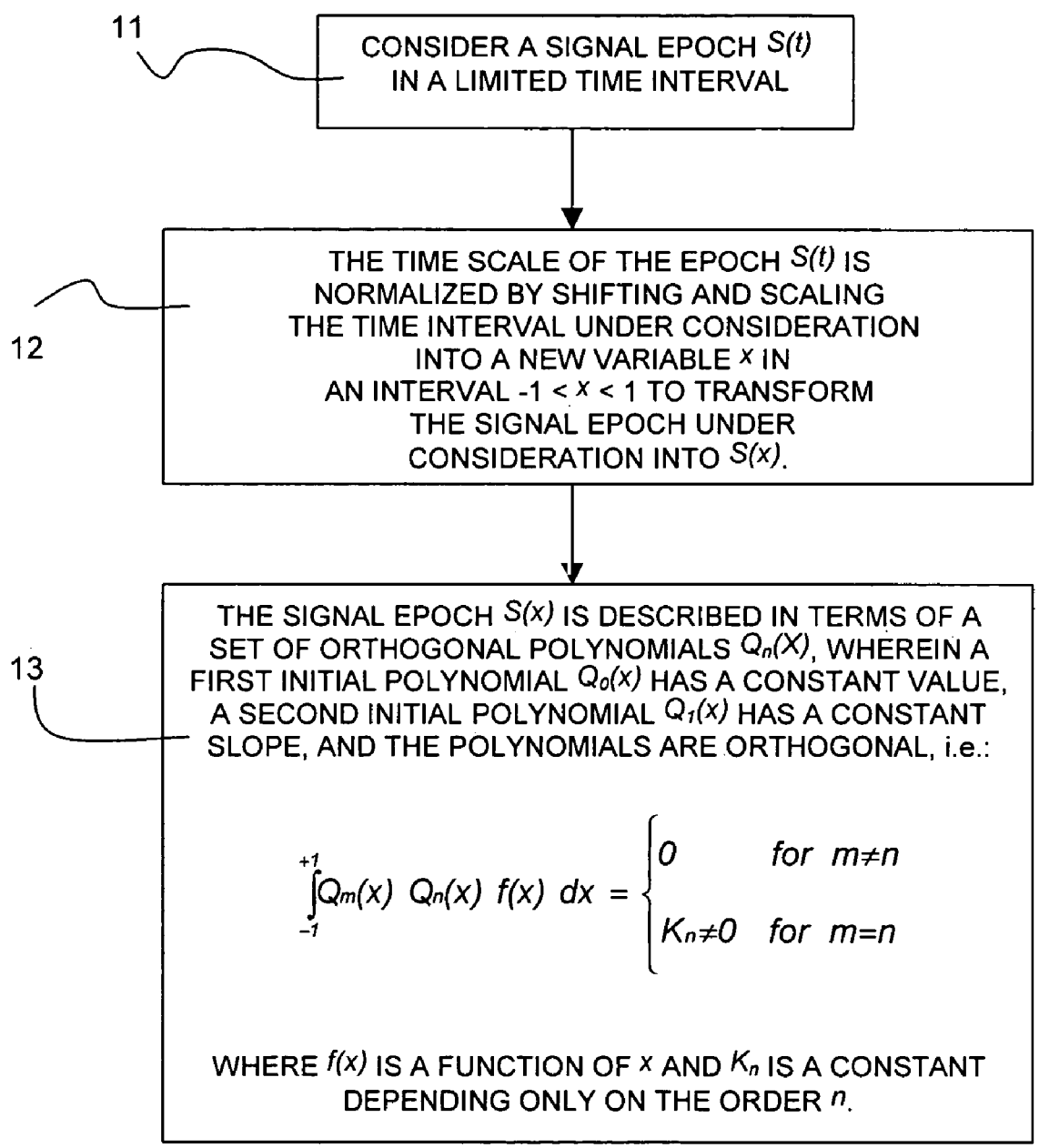
FIG. 1 is a schematic flow chart illustrating a technique according to a non-restrictive illustrative embodiment of the present invention, using orthogonal polynomials to model an input, contaminated signal.

From the analysis of the EMG signals, ECG signals, movement induced disturbances, background noise, and interference from the mains made in the "background of the invention" of the present specification, the following conclusions can be drawn:

The "a priori" knowledge of the input signal could be used for designing the filtering technique. One example is the interference from the mains, which has substantially sinusoidal shape and fixed frequency.

The filtering technique could model the disturbances, offsets, trends, noise, etc., in a more efficient manner than the Fourier transform is capable of. Other functions requiring a smaller set of terms could be used to more efficiently model the essential features of the signal.

DC components could be removed from finite length epochs since these components have frequencies lower than the lowest frequency associated to the epoch.

Trends could be removed from the signal. The reason for this time domain processing is that a ramp has a large number of harmonics when decomposed in the Fourier domain.

The frequency characteristics of the filtering technique could be preserved at higher frequencies in order to fully benefit from experiences of spectral filtering.

Since trigonometric functions do not fulfill the above requirements in the low frequency region of the spectrum, polynomials or other functions could be used to comply with the requirements associated to DC, ramp and oscillatory behaviour at higher frequencies.

Orthogonal sets of functions could be used in the filtering technique so that modifications of the filter components do not mutually influence each other.

Keeping the above in mind, the non-restrictive illustrative embodiments of the method and device according to the present invention are concerned with a filtering technique intended primarily for supplying filtered signals from contaminated signals of various kinds. Although this filtering technique could be used in a plurality of different applications, the illustrative embodiments relate to filtering of bioelectric signals.

More specifically, the description of the illustrative embodiments of the method and device in accordance with the present invention will focus on the filtering of EMG signals (wanted signal components) contaminated with ECG signals, movement induced disturbances, and background noise (unwanted signal components). The goal of the illustrative embodiments is to obtain a filtered EMG signal from a contaminated esophageal recording in view of controlling a mechanical ventilator.

Another possible application in the bioelectric field is to remove baseline variations (unwanted signal components) from ECG signals (wanted signal components) in view of obtaining immediate estimates of ST-depressions instead of averaging these ST-depressions over a number of QRS complexes, which delays the estimation process.

In yet another possible application, wanted signal components comprise internal variations of a QRS complex of an ECG signal and the unwanted signal components comprise a remaining part of the ECG signal. This enables investigation of internal variations of electric propagation within the heart muscle for the purpose of studying heart arrhythmia.

Filtering with Orthogonal Polynomials

A non-restrictive illustrative embodiment of the present invention proposes to use orthogonal, normalized polynomials to model the unwanted signal components in the contaminated signal. Once modeled, it is easier to remove the unwanted signal components from a contaminated input signal in order to obtain a corresponding, filtered signal substantially free from these unwanted signal components.

Another non-restrictive illustrative embodiment of the present invention is to model the wanted signal components and to use this model as an estimate of the filtered signal generally free from the unwanted signal components.

A non-restrictive illustrative embodiment of a method for modeling signal components of a contaminated signal will now be described.

Operation 11 (FIG. 1)

Referring to FIG. 1, let's consider a signal epoch S(t) in a limited time interval.

Operation 12 (FIG. 1)

The time scale of the epoch S(t) is normalized. For that purpose, the limited time interval under consideration is shifted and scaled into a new variable x in an interval −1<x<1. The signal epoch under consideration then becomes S(x).

Operation 13 (FIG. 1)

The signal epoch S(x) is described in terms of a set of orthogonal polynomials $Q_n(x)$. A first initial polynomial $Q_0(x)$ has a constant value, for example proportional to the DC component. A second initial polynomial $Q_1(x)$ has a constant slope, for example proportional to a trend. Thus:

$$Q_0(x) = \text{Constant} \quad (1)$$

and $$Q_1(x) = \text{Constant} \times x \quad (2)$$

Another condition requires the polynomials to be orthogonal, i.e. that:

$$\int_{-1}^{+1} Q_m(x)\, Q_n(x)\, f(x)\, dx = \begin{cases} 0 & \text{for } m \neq n \\ K_n \neq 0 & \text{for } m = n \end{cases} \quad (3)$$

where f(x) is a function of x and $K_n$ is a constant depending only on the order n.

The conditions given in equations (1) to (3) are fulfilled by several types of polynomials, which are orthogonal in the interval $-1 < x < 1$. Non-restrictive examples are the Legendre polynomials, Tchebyshev T-polynomials, and Tchebyshev U-polynomials.

Figure 2:
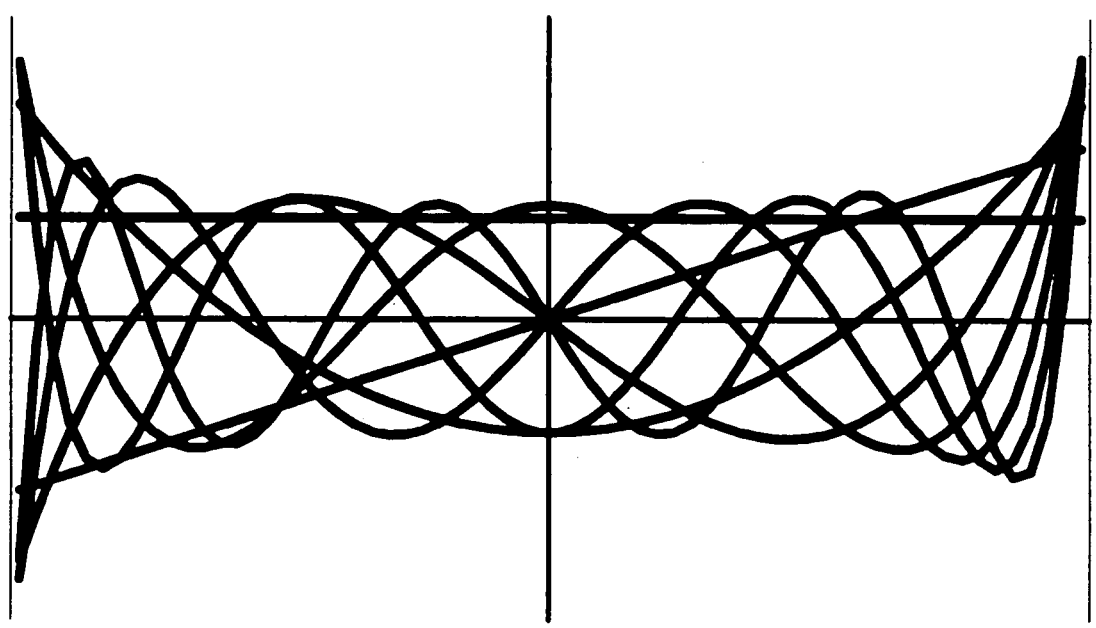
FIG. 2 illustrates, as an example, normalized Legendre orthogonal polynomials in an interval −1<x<1, of degrees zero (0) to seven (7) used for filtering finite length signal epochs.

As a non limitative example, FIG. 2 illustrates polynomials, orthogonal in the interval $-1 < x < 1$, of degrees zero (0) to seven (7) used for filtering finite length signal epochs. The functions in the plot of FIG. 2 are normalized Legendre polynomials.

The following Table 1 lists some of the properties of the above-mentioned Legendre polynomials, Tchebyshev T-polynomials, and Tchebyshev U-polynomials.

TABLE 1

Some characteristics of polynomials being orthogonal in the interval $-1 < x < 1$

| Type | f(x) | $K_n$ | $Q_0(x)$ | $Q_1(x)$ | $Q_2(x)$ | $Q_3(x)$ |
|---|---|---|---|---|---|---|
| Legendre | 1 | $2/(2n+1)$ | 1 | x | $(3x^2 - 1)/2$ | $(5x^3 - 3x)/2$ |
| Tchebyshev T | $(1 - x^2)^{-1/2}$ | $\pi/2$ (§) | 1 | x | $2x^2 - 1$ | $4x^3 - 3x$ |
| Tchebyshev U | $(1 - x^2)^{1/2}$ | $\pi$ | 1 | 2x | $4x^2 - 1$ | $8x^3 - 4x$ |

(§) $K_0 = \pi$. Also, in the synthesis (equation (4)), a factor of 0.5 is required for n=0.

The contaminated input signal can be synthesized from a sum of these polynomials:

$$S(x) = \sum_{n=0}^{\infty} C_n\, Q_n(x) \quad (4)$$

where $$C_n = \frac{1}{K_n} \int_{-1}^{+1} S(x) Q_n(x)\, f(x)\, dx \quad (5)$$

In practice, a limited number of terms is used. One reason is that terms of increasing order reflect increasing frequencies, which corresponds to regions containing little information.

The filtering technique can be conducted in accordance with different methods. The choice of the method will depend on the number of numeric calculations involved. Obviously, the longer the series of polynomials the more complicated the filtering procedure. For that reason, too long a series of polynomials will be avoided.

Figure 3:
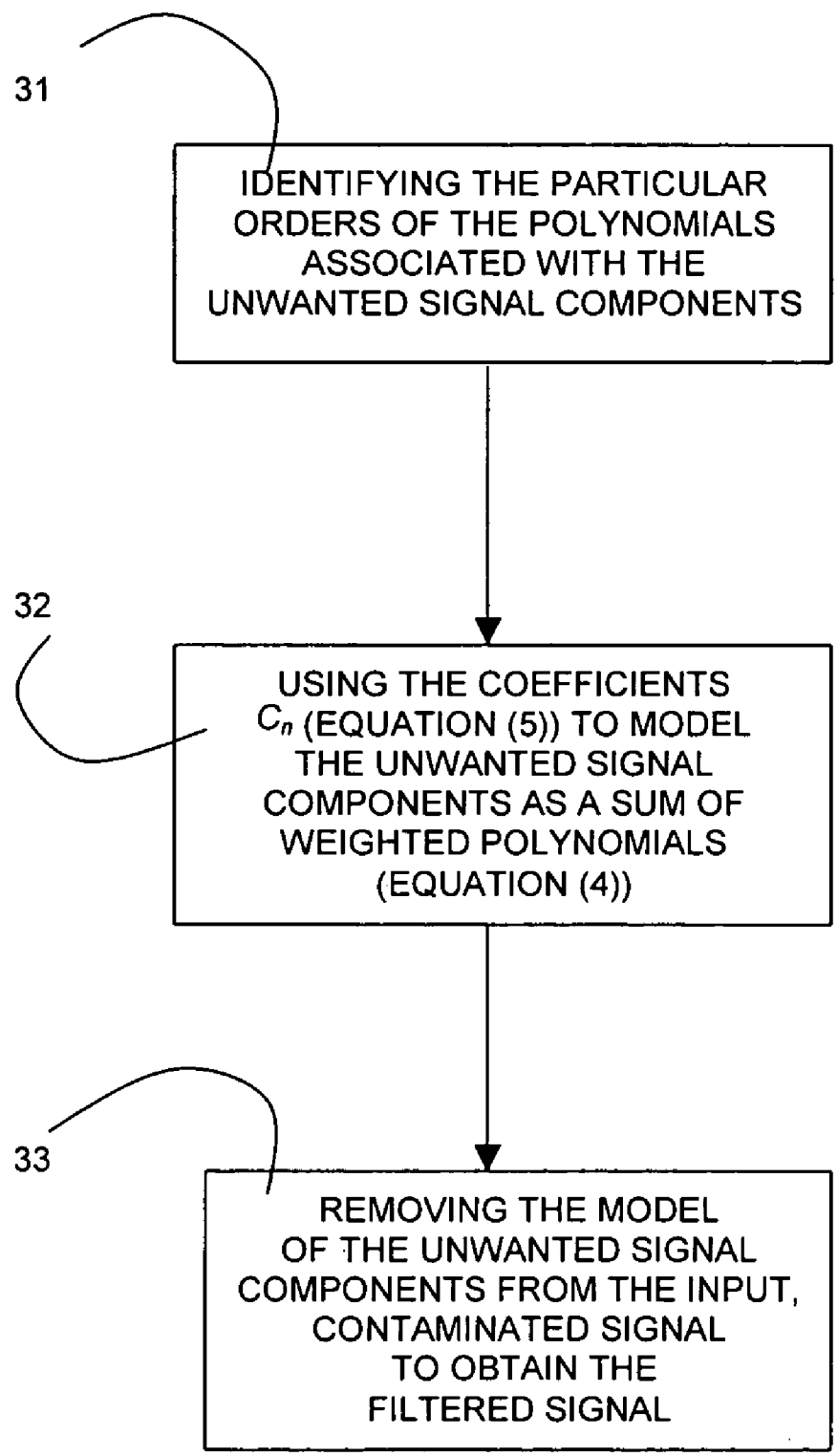
FIG. 3 is a schematic flow chart of a first method according to a non-restrictive illustrative embodiment of the present invention, for filtering an input signal having wanted signal components and unwanted signal components.

First Method (FIG. 3)

In accordance with a non-restrictive illustrative embodiment of the present invention, a first filtering method comprises the following operations:

1. The particular orders of the polynomials associated with the unwanted signal components are identified (Operation 31);
2. The unwanted signal components are modeled as a sum of polynomials (equation (4) and Operation 32) weighted by means of the coefficients $C_n$ (equation (5)); and
3. This model of the unwanted signal components is removed from the input, contaminated signal, more specifically from the other polynomials of the original set to obtain the filtered signal substantially free from these unwanted signal components (Operation 33).

Figure 4:
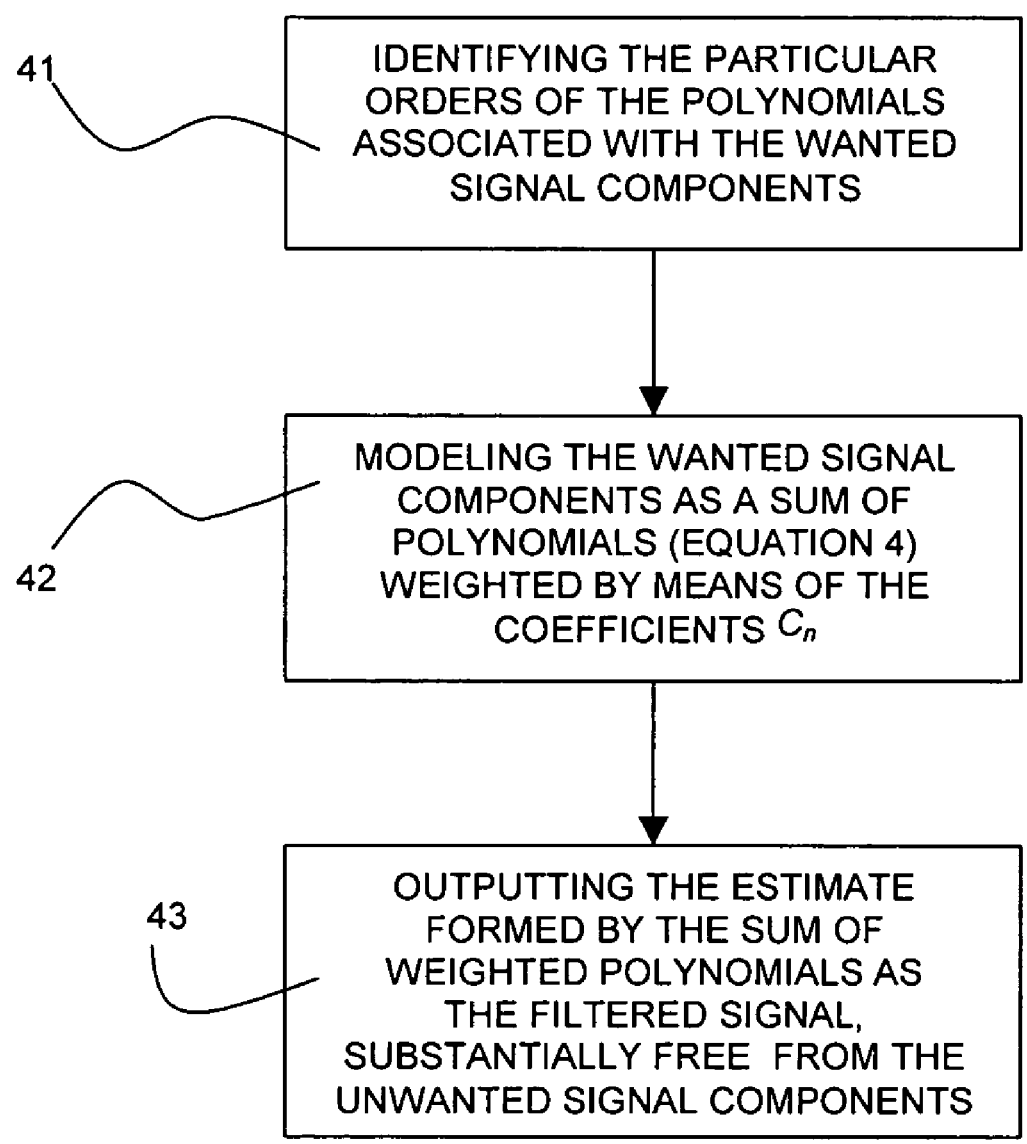
FIG. 4 is a schematic flow chart of a second method according to a non-restrictive illustrative embodiment of the present invention, for filtering an input signal having wanted signal components and unwanted signal components.

Second Method (FIG. 4)

In accordance with a non-restrictive illustrative embodiment of the present invention, a second filtering method comprises the following operations:

1. The particular orders of the polynomials of the set associated with the wanted signal components are identified (Operation 41);
2. The wanted signal components are modeled as a sum of polynomials (equation (4) and Operation 42) weighted by the coefficients $C_n$; and
3. The sum of weighted polynomials is outputted as an estimate of the filtered signal, substantially free from the unwanted signal components (Operation 43).

Figure 5:
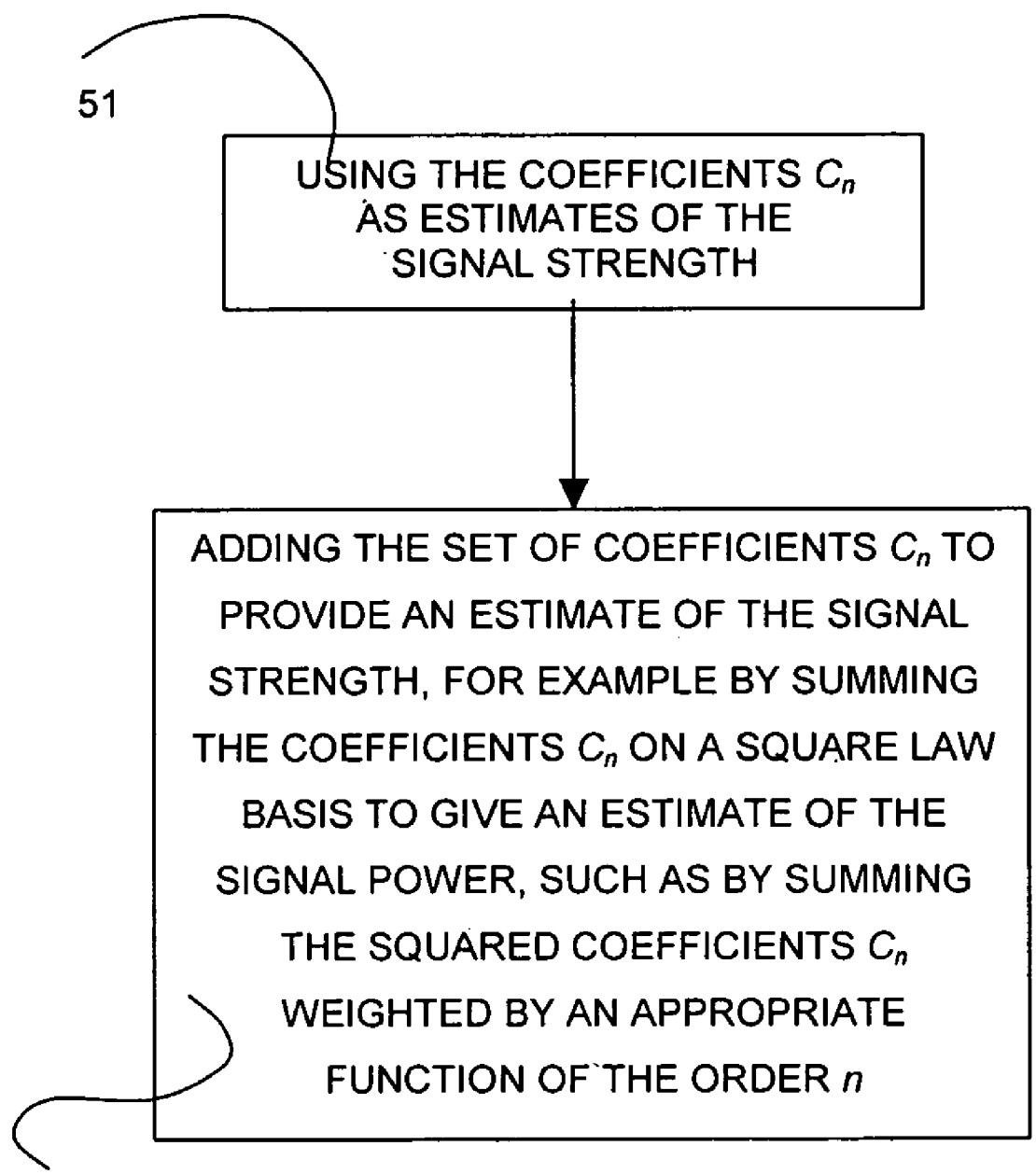
FIG. 5 is a schematic flow chart of a third method according to a non-restrictive illustrative embodiment of the present invention, for filtering an input signal having wanted signal components and unwanted signal components.

Third Method (FIG. 5)

This third method is used when only a representation of the strength of the signal is wanted. The third method can proceed according to the above-described second method (FIG. 4) while avoiding the signal synthesis (modeling of the wanted signal components as a sum of weighted polynomials as described in equation (4)), using instead the coefficients $C_n$ to model the strength of the wanted signal components.

More specifically, according to this third method:

1. The coefficients $C_n$, are used as estimates for the signal strength (Operation 51) to thereby model the strength of the wanted signal components.
2. The set of coefficients $C_n$ are then added to provide an estimate of the strength of the wanted signal components (Operation 52). As a non-restrictive illustrative example, the coefficients $C_n$ are summed on a square law basis to give an estimate of the signal power, for example by summing squared coefficients $C_n$. This summation on a square law basis is performed with additional weighting for the order n of the polynomial $Q_n$. In particular, for the Legendre polynomials, this weighting factor is $K_n$ and the square RMS value is given by:

$$RMS^2 = (1/2)\Sigma C_n^2 K_n$$

Corresponding constructions can be derived for other types of polynomials.

Those of ordinary skill in the art will appreciate that the RMS value of the synthesized signal according to equation (4) is equivalent to the summation of the coefficients $C_n$ on a square law basis followed by a square root calculation.

With an application of the non-restrictive illustrative embodiment of the filtering technique according to present invention to EMG signal processing, it has been observed that the polynomials of lowest orders mimic the baseline variations and polynomials of somewhat higher orders describe the ECG quite well. It has further been observed that the above-described second and third method automatically eliminate high frequency noise.

It should also be pointed out that Legendre polynomials of higher orders present an oscillatory behaviour thereby making it possible to obtain estimates for the dominating periodicity of the wanted signal components. The weighting coefficients $C_n$ are summed on a square law basis with a weighting proportional to the number of oscillations for the order n of the polynomial $Q_n$, normalized with respect to the sum of the weighting coefficients $C_n$ on a square law basis with polynomial order weighting $K_n$, in order to obtain the dominating periodicity of the wanted signal components. This provides an estimated number of oscillations (FRQ) in the signal interval $-1 \leq x \leq 1$:

$$FRQ = \frac{\sum C_n^2 K_n(n/2)}{\sum C_n^2 K_n}$$

Similar constructions can be derived for other types of polynomials.

Windowing to Remove Edge Effects

Equation (4) shows that an infinite number of polynomials are needed to fully represent the characteristics of the signal. If the summation is done over a limited number of polynomials, edge effects similar to those found in Fourier synthesis will occur. These edge effects are constituted by oscillations whose strength and frequency depend on the number of sinusoidal harmonic terms that are summated. More specifically, the edge effects can be described as being constituted by imperfections having a strength depending on the limited number of summated polynomials. The orthogonal polynomials, as described in Table 1 and illustrated in FIG. 2, attain large values at the opposite ends of the limited time interval. There is also a shift in sign between polynomials of adjacent orders at $x=-1$.

Figure 6:
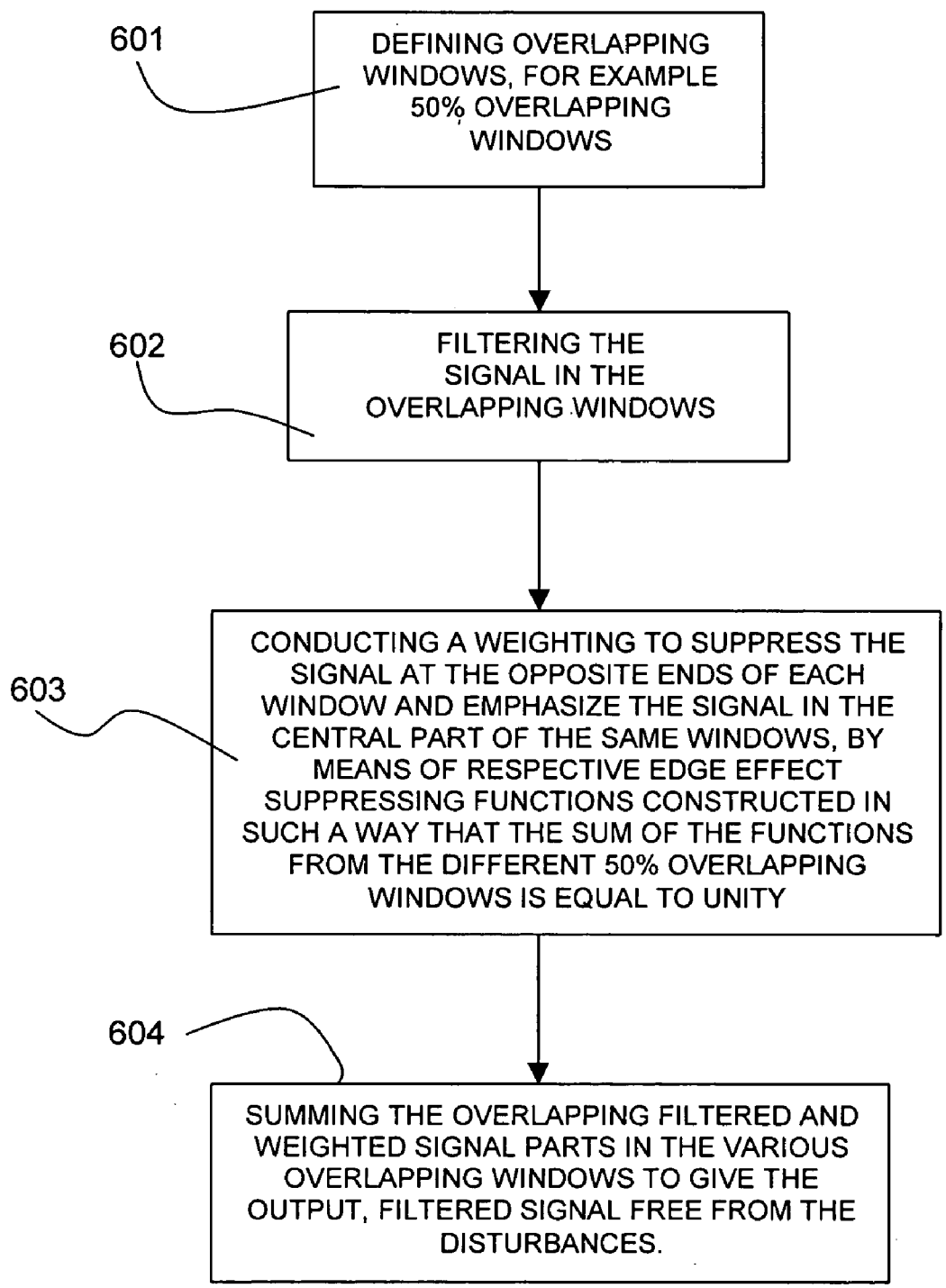
FIG. 6 is a schematic flow chart of a technique according to a non-restrictive, illustrative embodiment of the present invention, for eliminating edge effects.

These edge effects may have a large influence on the filtered signal and have to be considered. To suppress the influence of the edge effects on the filtered signal the following edge effect removal method according to a non-restrictive illustrative embodiment of the present invention can be used:

Operation 601 (FIG. 6)

Overlapping windows are first defined. As a non-limitative example, 50% overlapping windows such as odd windows 74 and even windows 75 of FIG. 7 can be used. Although the example of FIG. 7 uses 50% overlapping windows, it is within the scope of the present invention to use many other types of suitable overlapping windows.

Operation 602 (FIG. 6)

Figure 7:
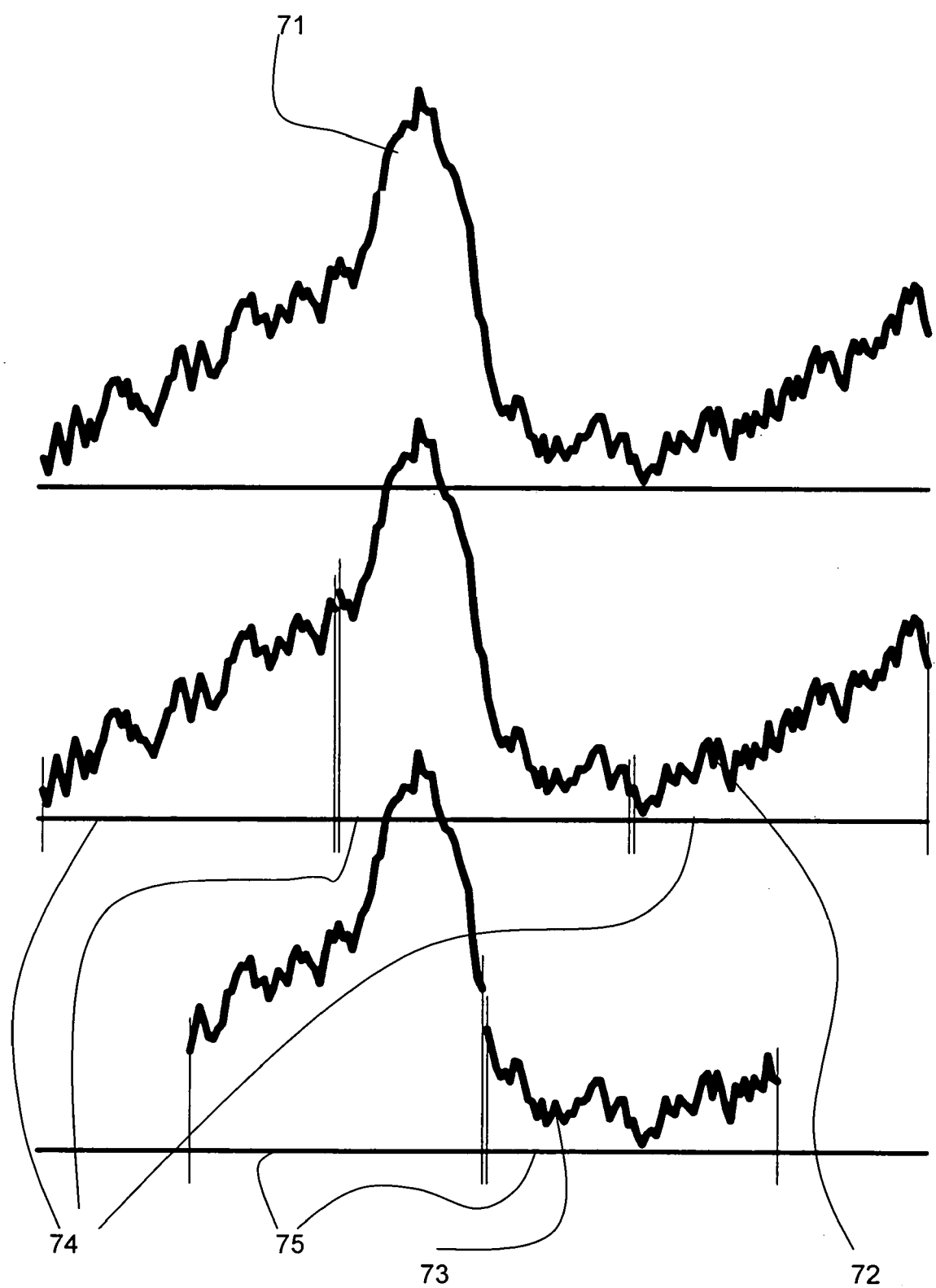
FIG. 7 illustrates a non-restrictive example of contaminated input signal (upper trace) splitted into overlapping windows, including odd windows (middle trace) and even windows (lower trace)

Filtering in accordance with one of the above-described methods is conducted in the overlapping windows, for example the windows 74 and 75 in FIG. 7.

Operation 603 (FIG. 6)

A weighting is conducted to suppress the signal at the opposite ends of each window and emphasize the signal in the central part of the same windows.

Figure 10:
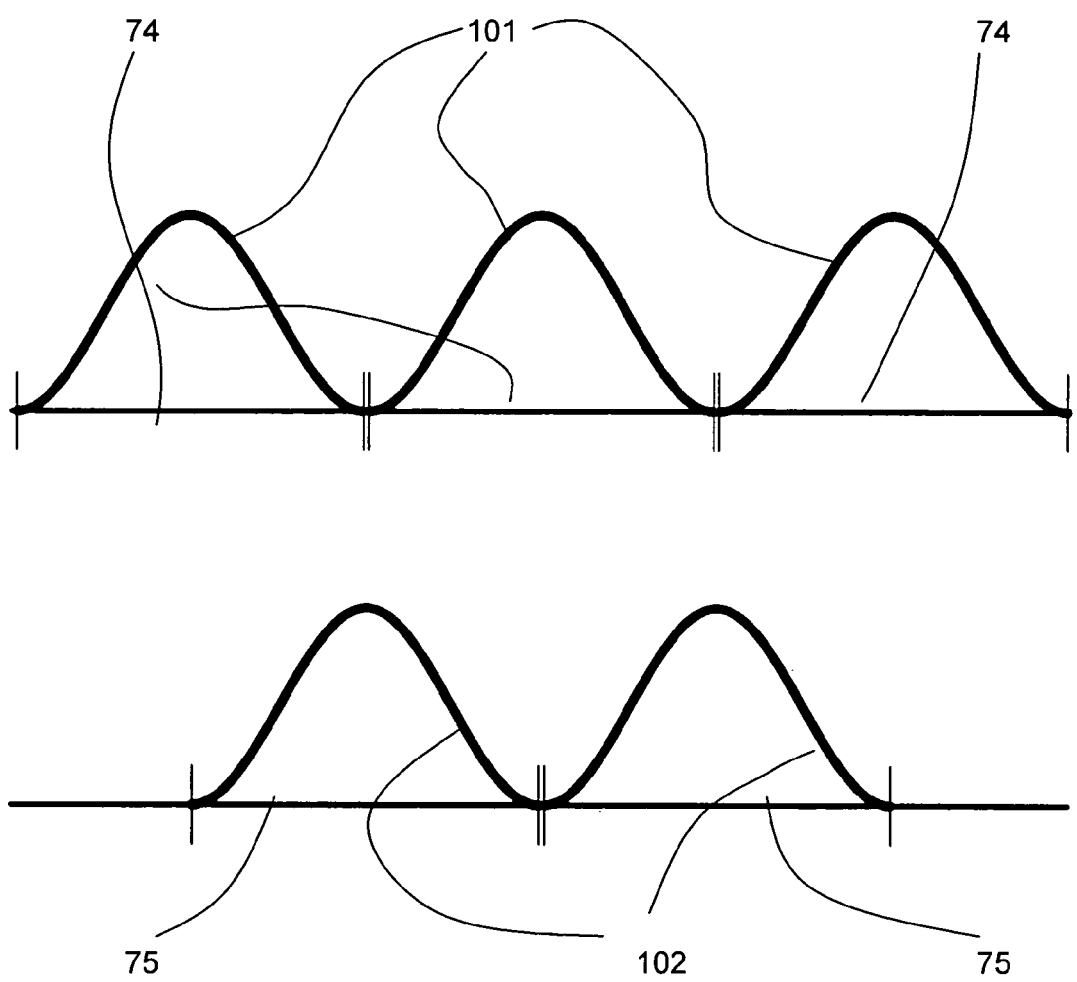
FIG. 10 illustrates non-limitative examples of edge effect suppressing functions in the respective odd and even windows of FIG. 7.

In the non-restrictive, illustrative embodiment of the filtering technique according to the present invention, the signal weighting is conducted in the various windows by means of respective edge effect suppressing functions constructed in such a way that the sum of the functions from the different overlapping windows is equal to unity (see for example functions 101 and 102 of FIG. 10).

In a non-restrictive illustrative embodiment of the present invention, since the sum of the weighting function for windows 74 and the weighting function for windows 75 is equal to unity, and the value of the weighting functions at the opposite ends of the respective windows is equal to zero in order to suppress the edge effects, the following conditions are met for such a weighting window:

$$W(x=-1) = W(x=+1) = 0 \quad (6)$$

and $$W(x) + W(1-x) = 1 \quad (7)$$

This implies that $$W(0) = 1 \quad (8)$$

and $$W(-x) = W(x) \quad (9)$$

There are a number of functions capable of fulfilling these conditions. Two might be mentioned: a triangular function (equation (10a)) and a squared cosine function (equation (10b)).

$$W(x) = 1 - |x| \quad (10a)$$

$$W(x) = \cos^2(\pi x/2) \quad (10b)$$

The function of equation (10b) presents the characteristics of having continuous derivatives and to suppress the signal more efficiently at the opposite ends of the window.

Operation 604 (FIG. 6)

The overlapping signal parts (see for example signal parts 111 and 112 of FIG. 11) are then summated to give the output, filtered signal (see for example signal 122 of FIG. 12) free from the unwanted signal components.

EXAMPLE (FIGS. 7–12)

A non-limitative example, corresponding to a combination of the first filtering method (FIG. 3) and windowing (FIG. 6), will now be described with reference to FIGS. 7–12.

Referring to FIG. 7, the input contaminatied signal (upper trace 71) is splitted into 50% overlapping windows such as 74 and 75 numbered in sequence order, including odd windows 74 (middle trace 72), and even windows 75 (lower trace 73).

Figure 8:
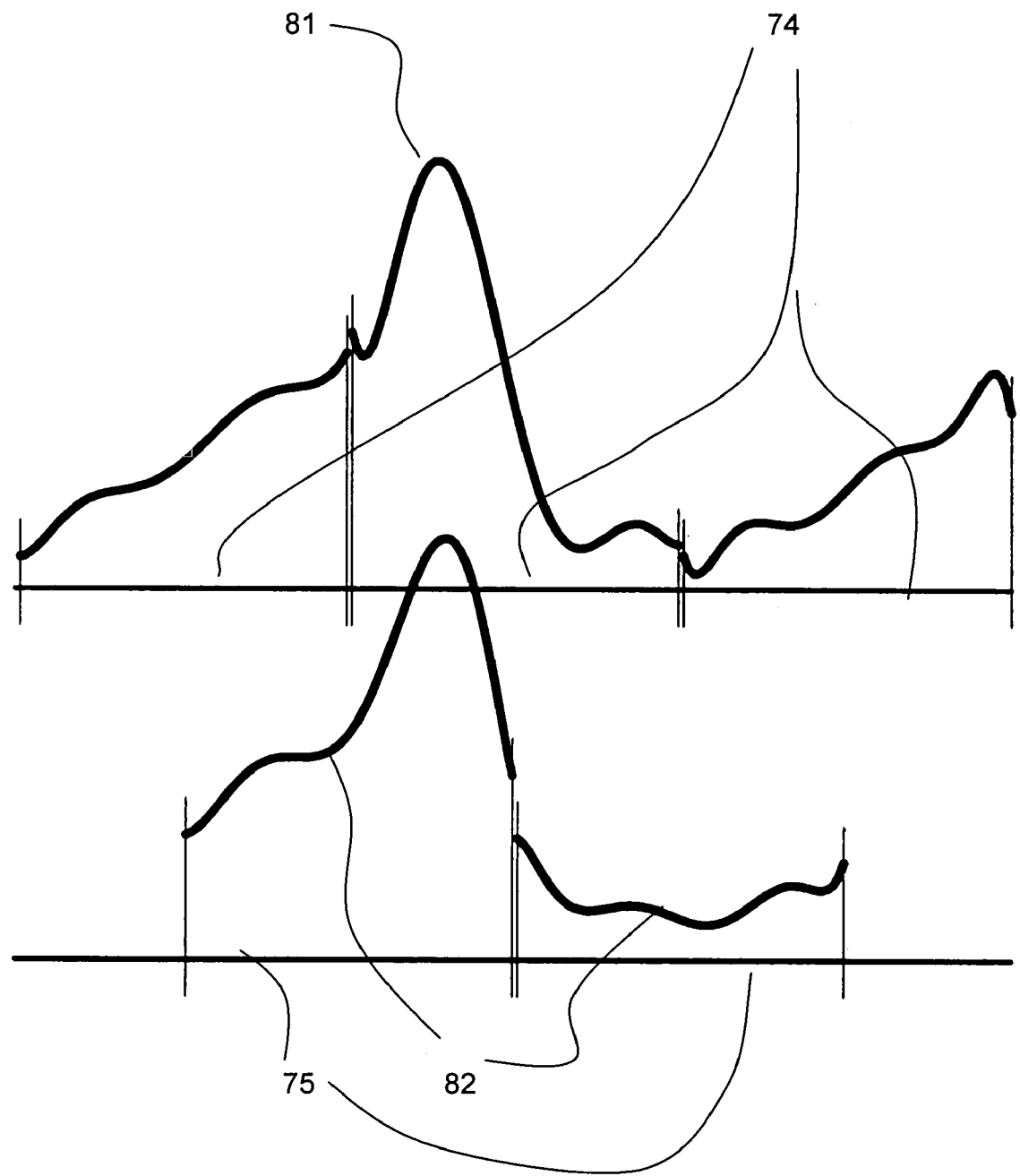
FIG. 8 is a non-limitative example of unwanted signal components modeled in the odd and even windows of FIG. 7 by signals synthesized from Legendre polynomials of orders zero (0) to seven (7)

In this non-limitative example, as illustrated in FIG. 8, the unwanted signal components in the middle 72 and lower 73 traces of FIG. 7 are modeled in every window 74 and 75 as signals 81 and 82, respectively, synthesized from Legendre polynomials of orders zero (0) to seven (7).

Figure 9:
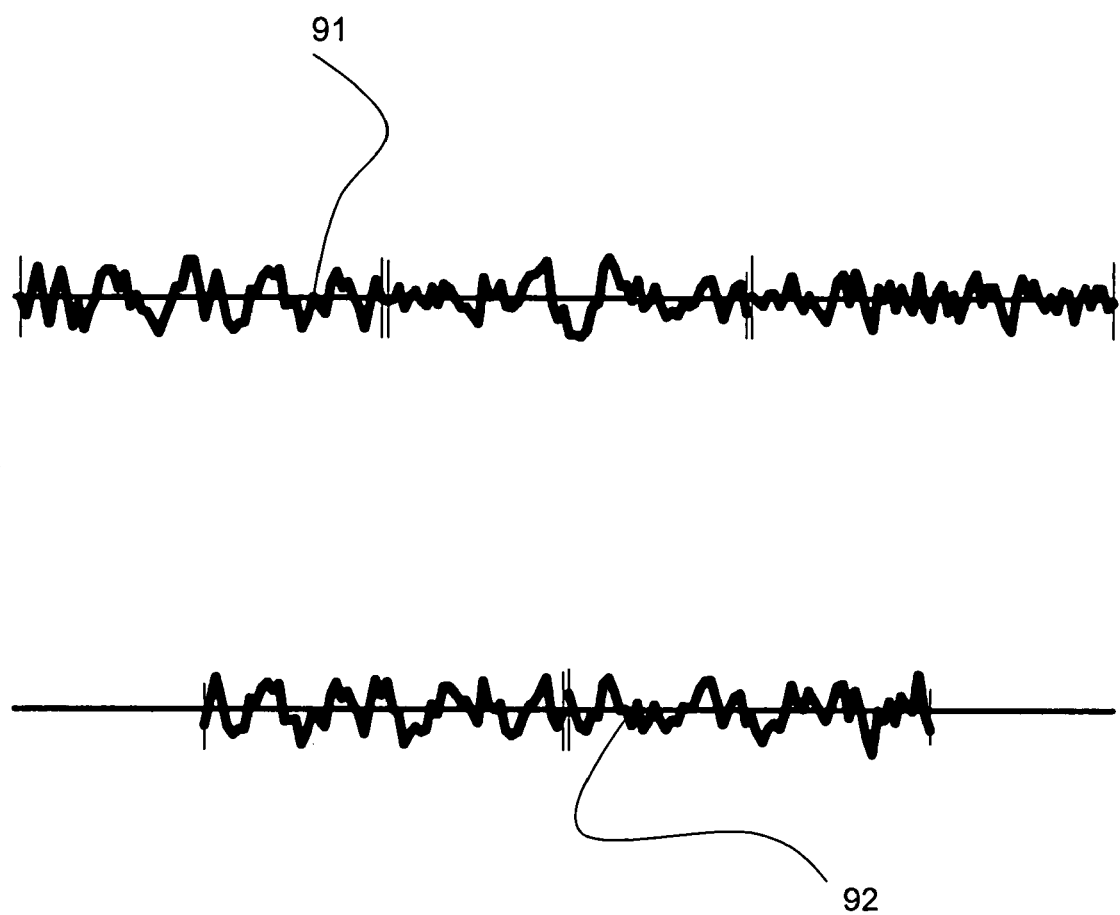
FIG. 9 are examples of signal parts remaining after removal from the input signal of the signals of FIG. 8, modeling the unwanted signal components.

FIG. 9 shows the signal parts 91 remaining after removal of the signal 81 (FIG. 8) in the odd windows 74 (middle trace 72) of FIG. 7. In the same manner, FIG. 9 shows the signal parts 92 remaining after removal of the signal 82 (FIG. 8) in the even windows 75 (lower trace 73) of FIG. 7.

FIG. 10 illustrates an edge effect suppressing function 101, corresponding to equation (10b), in each odd window 74 for smoothing transitions from one odd window 74 to the other. In the same manner, FIG. 10 illustrates an edge effect suppressing function 102, corresponding to equation (10b), in each even window 77 for smoothing transitions from one even window 75 to the other.

Figure 11:
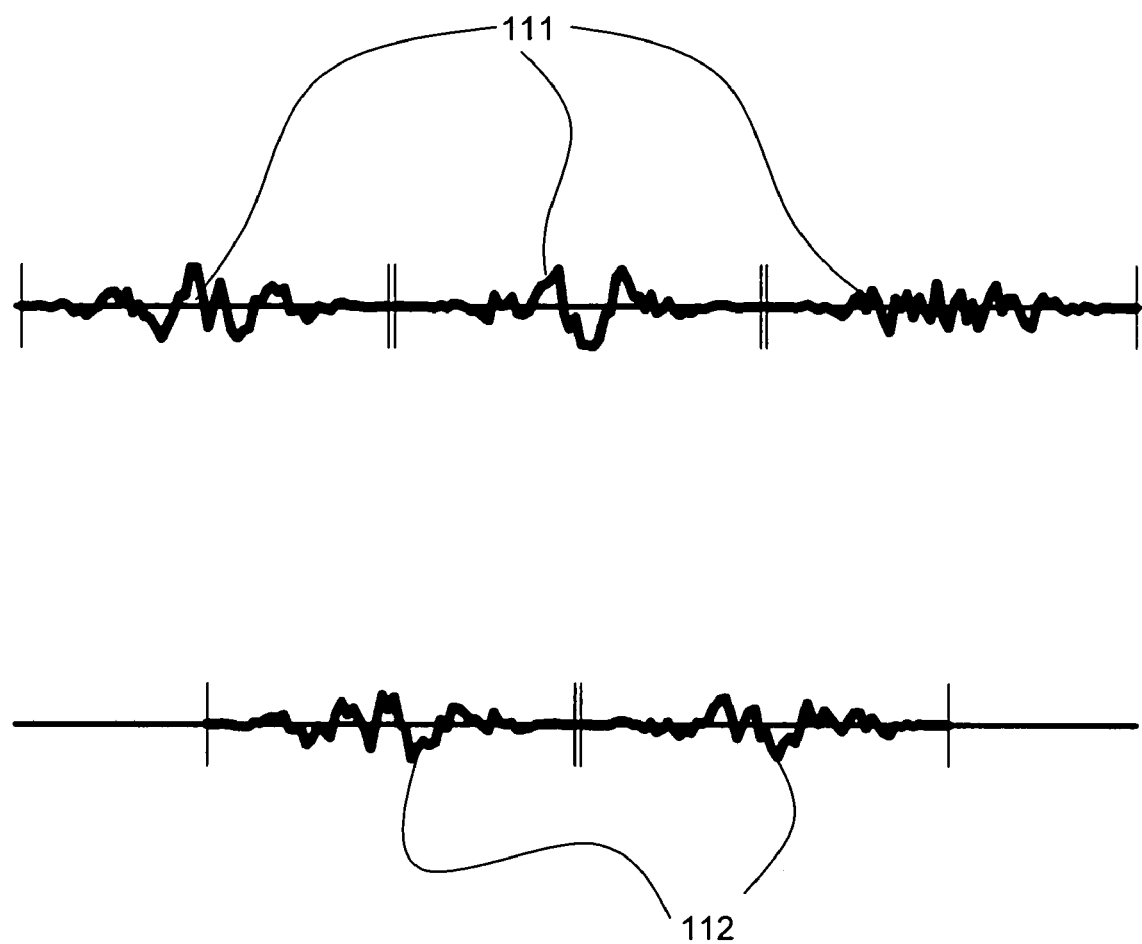
FIG. 11 are examples of weighted signal parts obtained by multiplying the signal parts of FIG. 9 with the edge effect suppressing functions in the respective odd and even windows of FIG. 7.
Figure 12:
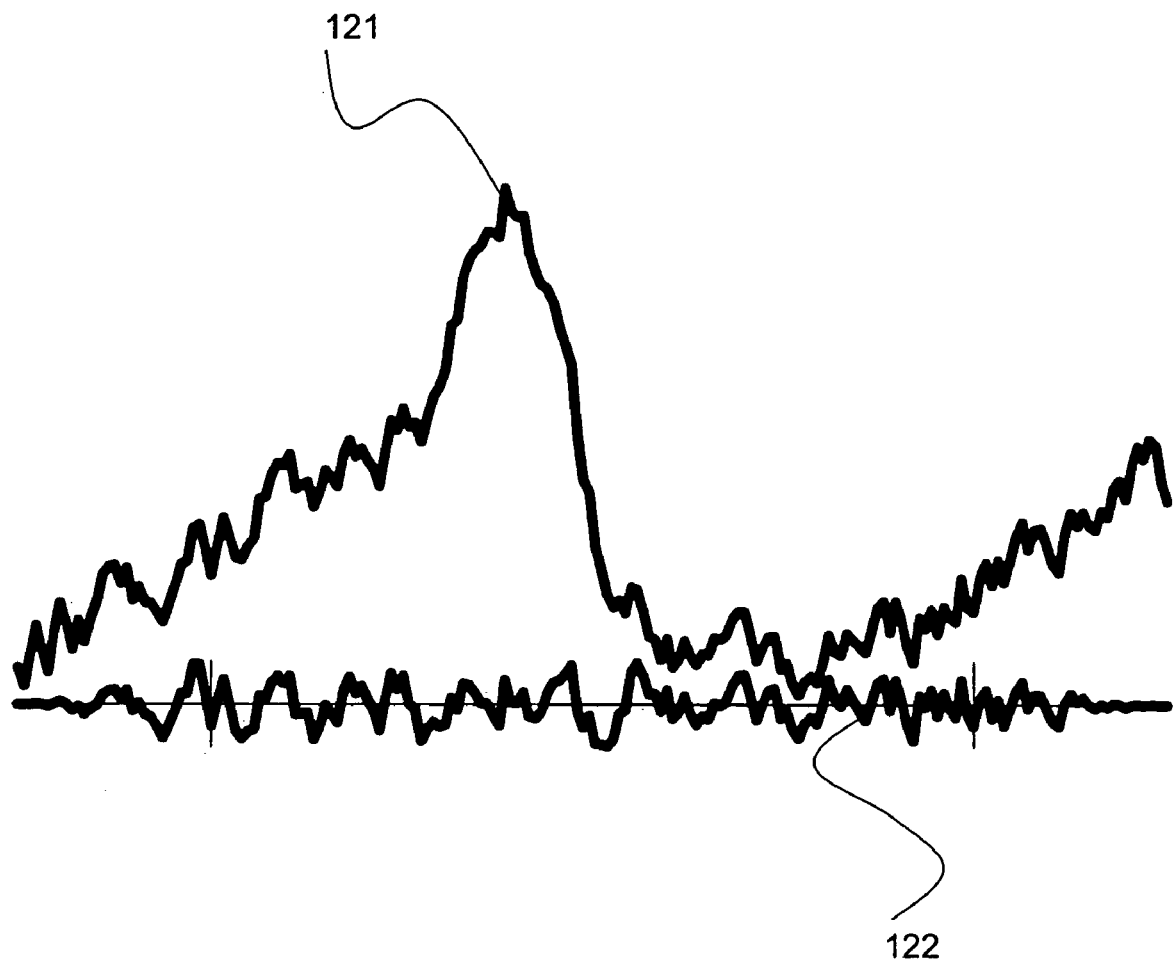
FIG. 12 are examples of the input contaminated signal (upper trace) and the filtered signal (lower trace) obtained by summing the weighted signal part of the various overlapping windows.

In FIG. 11, the signal parts 111 of the odd windows are obtained by multiplying the remaining signal parts 91 of FIG. 9 by the edge effect suppressing function 101 of the odd windows 74. In the same manner, the signal parts 112 (even windows) of FIG. 12 are obtained by multiplying the remaining signal parts 92 of FIG. 9 by the edge effect suppressing function 102 of the even windows 75. Multiplication of the remaining signal parts 91 by the function 101 has the effect of suppressing the above-described edge effects related to the odd windows 74. In the same manner, multiplication of the remaining signal parts 92 by the function 102 has the effect of suppressing the above-described edge effects related to the even windows 75.

Finally, in FIG. 12, the upper trace 121 corresponds to the input contaminated signal to be filtered as illustrated in the upper trace 71 of FIG. 7. The lower trace 122 of FIG. 12 is the processed signal from which the unwanted signal components have been filtered out, and corresponds to the summation of signal parts 111 (corresponding to the odd windows 74) and 112 (corresponding to the even windows 75) of FIG. 11.

Although the present invention has been described hereinabove in connection with illustrative embodiments thereof, these illustrative embodiments can be modified at will, within the scope of the appended claims without departing from the spirit and nature of the present invention.

What is claimed is:

1. A method of filtering an EMG input signal contaminated by a disturbance signal, the filtering method comprising:
    modeling the disturbance signal as polynomials of lower orders; and;
    removing the disturbance signal by removing the polynomials of lower orders from the contaminated EMG input signal to thereby obtain an EMG input signal substantially free from the disturbance signal.

2. A method of filtering as defined in claim 1, wherein the disturbance signal comprises at least one signal selected from the group consisting of: ECG signals, movement induced disturbances, and background noise.

3. A method of filtering as defined in claim 1, wherein polynomials of lower orders comprise Legendre polynomials of orders from zero (0) to seven (7).

4. A method of filtering as defined in claim 1, wherein the polynomials of lower orders comprise at least one of Tchebychev T-polynomials and Tchebychev U-polynomials.

5. A method of filtering as defined in claim 1, further comprising modeling the contaminated EMG input signal as a set of polynomials and wherein removing the disturbance signal comprises removing the polynomials of lower orders from the set of polynomials modeling the contaminated EMG input signal to thereby obtain an EMG input signal substantially free from the disturbance signal.

6. A method of filtering an input signal containing wanted signal components and unwanted signal components, comprising:
    modeling the input signal as a set of polynomials;
    modeling the unwanted signal components with a number of polynomials from the set; and
    removing the unwanted signal components from the input signal by removing the number of polynomials modeling the unwanted signal components from the set of polynomials to thereby leave in the input signal only the wanted signal components;
    wherein modeling the input signal as a set of polynomials comprises:
        considering an epoch S(t) of the input signal in a limited time interval, said epoch S(t) having a time scale; and
        normalizing the time scale of the epoch S(t).

7. A method as defined in claim 6, wherein normalizing the time scale of the epoch S(t) comprises:
    shifting and scaling the limited time interval under consideration into a new variable x in an interval $-1<x<1$ whereby the signal epoch becomes S(x).

8. A method as defined in claim 7, wherein modeling the input signal as a set of polynomials comprises modeling the input signal as a set of orthogonal polynomials $Q_n(x)$.

9. A method as defined in claim 8, wherein the set of orthogonal polynomials $Q_n(x)$ comprises:
    a first initial polynomial $Q_0(x)$ having a constant value; and
    a second initial polynomial $Q_1(x)$ having a constant slope.

10. A method as defined in claim 8, wherein modeling the input signal as a set of polynomials comprise:
    expressing the input signal as a sum of the polynomials $Q_n(x)$:

$$S(x) = \sum_{n=0}^{P} C_n \, Q_n(x)$$

where P represents a limited number of terms, and $$C_n = \frac{1}{K_n} \int_{-1}^{+1} S(x) \, Q_n(x) \, f(x) \, dx$$

where f(x) is a function of x and $K_n$ is a constant depending on the order n.

11. A method as defined in claim 10, wherein modeling the unwanted signal components comprises:
    associating particular orders of the polynomials with the unwanted signal components; and
    modeling the unwanted signal components as a sum of the polynomials of said particular orders, comprising weighting the polynomials of said particular orders by means of the coefficients $C_n$.

12. A method as defined in claim 11, wherein removing the number of polynomials modeling the unwanted signal components from the set of polynomials comprises:
    removing the sum of weighted polynomials from the sum of polynomials $Q_n(x)$.

13. A method as defined in claim 6, wherein modeling the input signal as a set of polynomials comprises modeling the input signal as a set of orthogonal polynomials.

14. A method as defined in claim 13, comprising selecting the orthogonal polynomials from the group consisting of:

Legendre polynomials;
Tchebyshev T-polynomials; and
Tchebyshev U-polynomials.

15. A method as of filtering an input signal containing wanted signal components and unwanted signal components, comprising:
modeling the input signal as a set of polynomials;
modeling the unwanted signal components with a number of polynomials from the set; and
removing the unwanted signal components from the input signal by removing the number of polynomials modeling the unwanted signal components from the set of polynomials to thereby leave in the input signal only the wanted signal components;
wherein:
modeling the input signal as a set of polynomials comprises modeling the input signal as a sum of a limited number of polynomials; and
said method further comprises eliminating edge effects constituted by imperfections having a strength depending on the limited number of polynomials.

16. A method as defined in claim 15, wherein:
eliminating the edge effects comprises defining overlapping windows;
modeling the unwanted signal components comprises modeling, in each window, the unwanted signal components with a number of polynomials from the set;
removing the disturbance signal from the input signal comprises removing, in each window, the number of polynomials modeling the unwanted signal components from the set of polynomials to thereby produce in said window a filtered signal part; and
eliminating edge effects further comprises:
in each window, weighting the filtered signal part to suppress the filtered signal part at opposite ends of the window and emphasize the filtered signal part in the central portion of said window; and
summing the weighted filtered signal parts of the overlapping windows to form an output filtered signal generally free from edge effects.

17. A method as defined in claim 16, wherein defining overlapping windows comprises:
defining 50% overlapping windows.

18. A method as defined in claim 16, wherein weighting the filtered signal part in each window comprises:
providing for each window an edge effect suppressing function; and
in each window, multiplying the filtered signal part by the edge effect suppressing function of said window.

19. A method as defined in claim 18, wherein providing for each window an edge effect suppressing function comprises:
constructing an edge effect suppressing function in such a manner that:
a sum of the edge effect suppressing functions of the various overlapping windows is equal to unity; and
a value of the edge suppressing function at opposite ends of each window is equal to zero.

20. A method as defined in claim 19, comprising selecting the edge effect suppressing functions of the overlapping windows from the group consisting of: a triangular function and a squared cosine function.

21. A method of filtering an input signal containing wanted signal components and unwanted signal components, comprising:
modeling the input signal as a set of polynomials;
modeling the unwanted signal components with a number of polynomials from the set; and
removing the unwanted signal components from the input signal by removing the number of polynomials modeling the unwanted signal components from the set of polynomials to thereby leave in the input signal only the wanted signal components;
wherein modeling the input signal as a set of polynomials comprises:
using higher order polynomials that mimic an oscillatory pattern of the input signal.

22. A device for filtering an EMG input signal contaminated by a disturbance signal, the device comprising:
means for modeling the disturbance signal as polynomials of lower orders; and
means for removing the disturbance signal from the contaminated input signal, wherein the disturbance signal removing means comprises means for removing the polynomials of lower orders from the input signal to thereby obtain an EMG input signal substantially free from the disturbance signal.

23. A device as defined in claim 22, wherein the disturbance signal comprises at least one signal selected from the group consisting of: ECG signals, movement induced disturbances and background noise.

24. A device as defined in claim 22, wherein the polynomials of lower orders comprise Legendre polynomials of orders from zero (0) to seven (7).

25. A device as defined in claim 22, wherein the polynomials of lower orders comprise at least one of Tchebychev T-polynomials and Tchebychev U-polynomials.

26. A device as defined in claim 22, further comprising means for modeling the contaminated EMG input signal as a set of polynomials and wherein the means for removing the disturbance signal comprises means for removing the polynomials of lower orders from the set of signal substantially free from the disturbance signal.

27. A device for filtering an input signal containing wanted signal components and unwanted signal components, comprising:
means for modeling the input signal as a set of polynomials:
means for modeling the unwanted signal components with a number of polynomials of said set; and
means for removing the unwanted signal components from the contaminated input signal, wherein the unwanted signal components removing means comprises means for removing the number of polynomials modeling the unwanted signal components from the set of polynomials to thereby leave in the input signal only the wanted signal components;
wherein the input signal modeling means comprises:
means for considering an epoch S(t) of the input signal in a limited time interval, said epoch S(t) having a time scale; and
means for nonnalizing the time scale of the epoch S(t), wherein said time scale normalizing means comprises means for shifting and scaling the limited time interval under consideration into a new variable x in an interval $-1<x<1$ whereby the signal epoch becomes S(x).

28. A device as defined in claim 27, wherein the input signal modeling means comprises:
means for modeling the input signal as a set of orthogonal polynomials $Q_n(x)$.

29. A device as defined in claim 28, wherein the set of orthogonal polynomials $Q_n(x)$ comprises:
- a first initial polynomial $Q_0(x)$ having a constant value; and
- a second initial polynomial $Q_1(x)$ having a constant slope.

30. A device as defined in claim 29, wherein the input signal modeling means comprises:
- means for expressing the input signal as a sum of the polynomials $Q_n(x)$:

$$S(x) = \sum_{n=0}^{P} C_n \, Q_n(x)$$

where P represents a limited number of terms, and $$C_n = \frac{1}{K_n} \int_{-1}^{+1} S(x) \, Q_n(x) \, f(x) \, dx$$

where f(x) is a function of x and $K_n$ is a constant depending on the order n.

31. A device as defined in claim 30, wherein:
- the input signal modeling means comprises means for modeling the input signal as a sum of a limited number of polynomials; and
- said device further comprises means for eliminating edge effects constituted by imperfections having a strength depending on the limited number of polynomials.

32. A device as defined in claim 31, wherein:
- the edge effects eliminating means comprises means for defining overlapping windows;
- the means for modeling the unwanted signal components comprises means for modeling, in each window, the unwanted signal components with a number of polynomials of said set;
- the unwanted signal components removing means comprises means for removing, in each window, the number of polynomials modeling the unwanted signal components from the set of polynomials to thereby produce in said window a filtered signal part; and
- the edge effects eliminating means further comprises:
  - for each window, means for weighting the filtered signal part to suppress the filtered signal part at opposite ends of the window and emphasize the filtered signal part in the central portion of said window; and
  - means for summing the weighted filtered signal parts of the overlapping windows to form an output filtered signal generally free from edge effects.

33. A device as defined in claim 32, wherein the overlapping windows comprise 50% overlapping windows.

34. A device as defined in claim 32, wherein the filtered signal part weighting means comprises:
- means for providing for each window an edge effect suppressing function; and
- means for multiplying, in each window, the filtered signal part by the edge effect suppressing function of said window.

35. A method of filtering an EMG input signal contaminated by a disturbance signal, the filtering method comprising:
- modeling the EMG input signal polynomials of higher orders; and
- outputting the polynomials of higher orders as an estimate of the EMG input signal substantially free from the disturbance signal.

36. A method as defined in claim 35, wherein the disturbance signal comprises at least one of a cardiac signal, motion disturbance, and background noise.

37. A method as defined in claim 35, wherein modeling the EMG input signal as polynomials of higher orders comprises modeling said EMG input signal as orthogonal of higher orders.

38. A method as defined in claim 37, comprising selecting the orthogonal polynomials from the group consisting of:
- Legendre polynomials;
- Tchebyshev T-polynomials; and
- Tchebyshev U-polynomials. as orthogonal polynomials of higher orders.

39. A method as defined in claim 35, further comprising weighting the polynomials modeling the EMG input signal by means of weighting coefficients.

40. A method of filtering as defined in claim 35, wherein the disturbance signal comprises at least one signal selected from the group consisting of: ECG signals, movement induced disturbances and background noise.

41. A method of filtering an input signal containing wanted signal components and unwanted signal components, comprising:
- modeling the input signal as a set of polynomials;
- modeling the wanted signal components with a number of the polynomials of said set; and
- outputting the polynomials modeling the wanted signal components as an estimate of the input signal substantially free from the unwanted signal components;
- wherein modeling the input signal comprises:
  - considering an epoch S(t) of the signal in a limited time interval, said epoch S(t) having a time scale; and
  - normalizing the time scale of the epoch S(t).

42. A method as defined in claim 41, wherein normalizing the time scale of the epoch S(t) comprises:
- shifting and scaling the limited time interval under consideration into a new variable x in an interval $-1<x<1$ whereby the signal epoch becomes S(x).

43. A method as defined in claim 42, wherein modeling the input signal as a set of polynomials comprises modeling the input signal as a set of orthogonal polynomials $Q_n(x)$.

44. A method as defined in claim 43, wherein the set of orthogonal polynomials $Q_n(x)$ comprises:
- a first initial polynomial $Q_0(x)$ having a constant value; and
- a second initial polynomial $Q_1(x)$ having a constant slope.

45. A method as defined in claim 43, wherein modeling the input signal as a set of polynomials comprises:
- expressing the input signal as a sum of the polynomials $Q_n(x)$:

$$S(x) = \sum_{n=0}^{P} C_n \, Q_n(x)$$

where P represents a limited number of terms, and $$C_n = \frac{1}{K_n} \int_{-1}^{+1} S(x) \, Q_n(x) \, f(x) \, dx$$

where f(x) is a function of x and $K_n$ is a constant depending on the order n.

46. A method as defined in claim 45, wherein modeling the wanted signal components with a number of the polynomials of said set comprises:
   associating particular orders of the polynomials with the wanted signal components; and
   modeling the wanted signal components as a sum of the polynomials of said particular orders, comprising weighting the polynomials of said particular orders by means of the coefficients $C_n$.

47. A method of filtering an input signal containing wanted signal components and unwanted signal components, comprising:
   modeling the input signal as a set of polynomials;
   modeling the wanted signal components with a number of the polynomials of said set; and
   outputting the polynomials modeling the wanted signal components as an estimate of the input signal substantially free from the unwanted signal components;
      wherein modeling the input signal as a set of polynomials comprises:
         using higher order polynomials that mimic an oscillatory pattern of the input signal.

48. A method of filtering an input signal containing wanted signal components and unwanted signal components, comprising:
   modeling the input signal as a set of polynomials;
   modeling the wanted signal components with a number of the polynomials of said set; and
   outputting the number of polynomials modeling the wanted signal components as an estimate of the input signal substantially free from the unwanted signal components;
   wherein:
      modeling the input signal as a set of polynomials comprises modeling the input signal as a sum of a limited number of polynomials; and
      said method further comprises eliminating edge effects constituted by imperfections having a strength depending on the limited number of polynomials.

49. A method as defined in claim 48, wherein:
   eliminating the edge effects comprises defining overlapping windows;
   modeling the wanted signal components comprises modeling, in each window, the wanted signal components with a number of polynomials of said set;
   outputting the number of polynomials modeling the wanted signal components comprises outputting, for each window, the number of polynomials modeling the wanted signal components to thereby produce in said window a filtered signal part; and
   eliminating the edge effects further comprises:
   in each window, weighting the filtered signal part to suppress the filtered signal part at opposite ends of the window and emphasize the filtered signal part in the central part of said window; and
   summing the weighted filtered signal parts of the overlapping windows to form an output filtered signal generally free from edge effects.

50. A method as defined in claim 49, wherein defining overlapping windows comprises:
   defining 50% overlapping windows.

51. A method as defined in claim 49, wherein weighting the filtered signal part in each window comprises:
   providing for each window an edge effect suppressing function; and
   in each window, multiplying the filtered signal part by the edge effect suppressing function of said window.

52. A method as defined in claim 51, wherein providing for each window an edge effect suppressing function comprises:
   constructing an edge effect suppressing function in such a manner that:
   a sum of the edge effect suppressing functions of the various overlapping windows is equal to unity; and
   a value of the edge suppressing function at opposite ends of each window is equal to zero.

53. A method as defined in claim 51, comprising selecting the edge effect suppressing functions of the overlapping windows from the group consisting of: a triangular function and a squared cosine function.

54. A device for filtering an EMG input signal contaminated by a disturbance signal, the device comprising:
   means for modeling the EMG input signal polynomials of higher orders; and
   means for outputting the polynomials of higher orders as an estimate of the EMG input signal substantially free from the disturbance signal.

55. A device for filtering an input signal containing wanted signal components and unwanted signal components, comprising:
   means for modeling the input signal as a set of polynomials:
   means for modeling the wanted signal components with a number of the polynomials of said set; and
   means for outputting the polynomials modeling the wanted signal components as an estimate of the input signal substantially free from the unwanted signal components;
      wherein the input signal modeling means comprises:
      means for considering an epoch S(t) of the signal in a limited time interval, said epoch S(t) having a time scale; and
      means for normalizing the time scale of the epoch S(t), wherein said time scale normalizing means comprises means for shifting and scaling the limited time interval under consideration into a new variable x in an interval $-1<x<1$ whereby the signal epoch becomes S(x).

56. A device as defined in claim 55, wherein the input signal modeling means comprises:
   means for modeling said input signal as a set of orthogonal polynomials $Q_n(x)$.

57. A device as defined in claim 56, wherein the set of orthogonal polynomials $Q_n(x)$ comprises:
   a first initial polynomial $Q_0(x)$ having a constant value; and
   a second initial polynomial $Q_1(x)$ having a constant slope.

58. A device as defined in claim 57, wherein the input signal modeling means comprises:
   means for expressing the input signal as a sum of the polynomials $Q_n(x)$:

$$S(x) = \sum_{n=0}^{P} C_n \, Q_n(x)$$

where P represents a limited number of terms, and $$C_n = \frac{1}{K_n} \int_{-1}^{+1} S(x) \, Q_n(x) \, f(x) \, dx$$

where f(x) is a function of x and $K_n$ is a constant depending on the order n.

59. A device as defined in claim 58, wherein:
the input signal modeling means comprises means for modeling the input signal as a sum of a limited number of polynomials; and
said device further comprises means for eliminating edge effects constituted by imperfections having a strength depending on the limited number of polynomials.

60. A device as defined in claim 59, wherein:
the edge effects eliminating means comprises means for defining overlapping windows;
the means for modeling the wanted signal components comprises means for modeling, in each window, the wanted signal components with a number of the polynomials of said set;
the polynomials outputting means comprises means for outputting, for each window, the polynomials modeling the wanted signal components to thereby produce in said window a filtered signal part; and
the edge effects eliminating means further comprises:
for each window, means for weighting the filtered signal part to suppress the filtered signal part at opposite ends of the window and emphasize the filtered signal part in a central portion of said window; and
means for summing the weighted filtered signal parts of the overlapping windows to form an output filtered signal generally free from edge effects.

61. A device as defined in claim 60, wherein the overlapping windows comprise 50% overlapping windows.

62. A device as defined in claim 60, wherein the filtered signal part weighting means comprises:
means for providing for each window an edge effect suppressing function; and
means for multiplying, in each window, the filtered signal part by the edge effect suppressing function of said window.

63. A method of filtering an input signal containing wanted signal components and unwanted signal components, comprising:
modeling the input signal as a set of polynomials;
determining, for each polynomial, a weighting coefficient indicative of signal strength; and
summing the weighting coefficients to provide an estimate of the strength of the wanted signal components;
wherein summing the weighting coefficients comprises:
summing the weighting coefficients on a square law basis with polynomial order weighting to give an estimate of a power of the wanted signal components.

64. A method as defined in claim 63, wherein determining, for each polynomial, a weighting coefficient indicative of signal strength comprises:
modeling the strength of the wanted signal components through the weighting coefficients.

65. A method of filtering an input signal containing wanted signal components and unwanted signal components, comprising:

modeling the input signal as a set of polynomials;
determining, for each polynomial a weighting coefficient indicative of signal strength; and
summing the weighting coefficients to provide an estimate of the strength of the wanted signal components:
wherein summing the weighting coefficients comprises:
calculating a sum of the weighting coefficients on a square law basis with a weighting proportional to the number of oscillations for the order of the polynomial, normalized with respect to the sum of the weighting coefficients on a square law basis with polynomial order weighting, in order to obtain a dominating periodicity of the wanted signal components.

66. A method of filtering an input signal containing wanted signal components and unwanted signal components, comprising:
modeling the input signal as a set of polynomials:
determining, for each polynomial, a weighting coefficient indicative of signal strength; and
summing the weighting coefficients to provide an estimate of the strength of the wanted signal components;
wherein modeling the input signal as a set of polynomials comprises:
considering an epoch S(t) of the input signal in a limited time interval, said epoch S(t) having a time scale; and
normalizing the time scale of the epoch S(t).

67. A method as defined in claim 66, wherein normalizing the time scale of the epoch S(t) comprises:
shifting and scaling the limited time interval under consideration into a new variable x in an interval −1<x<1 whereby the signal epoch becomes S(x).

68. A method as defined in claim 67, wherein modeling the input signal as a set of polynomials comprises modeling the signal as a set of orthogonal polynomials $Q_n(x)$.

69. A method as defined in claim 68, comprising selecting the orthogonal polynomials from the group consisting of:
Legendre polynomials;
Tchebyshev T-polynomials; and
Tchebyshev U-polynomials.

70. A method as defined in claim 68, wherein modeling the input signal as a set of polynomials comprises:
expressing the input signal as a sum of the polynomials $Q_n(x)$:

$$S(x) \sum_{n=0}^{P} C_n \, Q_n(x)$$

where P represents a limited number of terms, and $$C_n = \frac{1}{K_n} \int_{-1}^{+1} S(x) \, Q_n(x) \, f(x) \, dx$$

where f(x) is a function of x and $K_n$ is a constant depending on the order n,
wherein the terms $C_n$ constitute said weighting factors.

71. A device for filtering an input signal containing wanted signal components and unwanted signal components, comprising:
means for modeling the input signal as a set of polynomials;

means for determining, for each polynomial, a weighting factor indicative of signal strength; and means for summing the weighting coefficients to provide an estimate of the strength of the wanted signal components;

wherein the weighting coefficients summing means comprises:

means for summing the weighting coefficients on a square law basis with polynomial order weighting to give an estimate of a power of the EMG input signal substantially free from the disturbance signal.

72. A device as defined in claim 71, wherein the determining means comprises:

means for modeling the strength of the wanted signal components through the weighting coefficients.

73. A device for filtering an input signal containing wanted signal components and unwanted signal components, comprising:

means for modeling the input signal as a set of polynomials;

means for determining, for each polynomial, a weighting factor indicative of signal strength; and means for summing the weighting coefficients to provide an estimate of the strength of the wanted signal components;

wherein the means for summing the weighting coefficients comprises:

means for calculating a sum of the weighting coefficients on a square law basis with a weighting proportional to the number of oscillations for the order of the polynomial, normalized with respect to the sum of the weighting coefficients on a square law basis with polynomial order weighting, in order to obtain a dominating periodicity of the input signal.

74. A device for filtering an input signal containing wanted signal components and unwanted signal components, comprising:

means for modeling the input signal as a set of polynomials;

means for determining, for each polynomial, a weighting factor indicative of signal strength; and means for summing the weighting coefficients to provide an estimate of the strength of the wanted signal components;

wherein the input signal modeling means comprises:

means for considering an epoch S(t) of the input signal in a limited time interval, said epoch S(t) having a time scale; and means for normalizing the time scale of the epoch S(t).

75. A device as defined in claim 74, wherein the time scale normalizing means comprises:

means for shifting and scaling the limited time interval under consideration into a new variable x in an interval −1<x<1 whereby the signal epoch becomes S(x).

76. A device as defined in claim 75, wherein the input signal modeling means comprises means for modeling the signal as a set of orthogonal polynomials $Q_n(x)$.

77. A device as defined in claim 76, wherein the input signal modeling means comprises:

means for expressing the input signal as a sum of the polynomials $Q_n(x)$:

$$S(x) \sum_{n=0}^{P} C_n \, Q_n(x)$$

where P represents a limited number of terms, and $$C_n = \frac{1}{K_n} \int_{-1}^{+1} S(x) \, Q_n(x) \, f(x) \, dx$$

where f(x) is a function of x and $K_n$ is a constant depending on the order n, wherein the terms $C_n$ constitute said weighting factors.

* * * * *

UNITED STATES PATENT AND TRADEMARK OFFICE
CERTIFICATE OF CORRECTION

PATENT NO. : 7,221,975 B2  Page 1 of 1
APPLICATION NO. : 10/728081
DATED : May 22, 2007
INVENTOR(S) : Lindstrom It is certified that error appears in the above-identified patent and that said Letters Patent is hereby corrected as shown below:

Column 8, line 57, after the words "coefficient Cn" delete ",".
Column 9, line 13, after the words "according to" insert the word --the--.
Column 10, line 60, the word "contaminatied" should read --contaminated--.
In col. 11 claim 1, line 46, after the word "and" delete ";".
In col. 11 claim 4, lines 59-60, each occurrence of the word "Tchebychev" should read --Tchebyshev--.
In col. 12 claim 10, line 32, replace the word "comprise" with --comprises--.
In col. 13 claim 15, line 4, after the word "method" deleted the word "as".
In col. 14 claim 25, lines 31-32, each occurrence of the word "Tchebychev" should read --Tchebyshev--.
In col. 14 claim 26, line 38, after the words "from the set of" insert the words --polynomials modeling the contaminated EMG input signal to thereby obtain an EMG input--.
In col. 14 claim 27, line 58, the word "nonnalizing" should read --normalizing--.
In col. 15 claim 35, line 66, after the word "signal" insert the word --as--.
In col. 16 claim 38, lines 15-16, after the period, the words "as orthogonal polynomials of higher orders" should be deleted.
In col. 18 claim 54, line 20, after the word "signal" insert the word --as--.

Signed and Sealed this

Twenty-third Day of October, 2007

JON W. DUDAS
*Director of the United States Patent and Trademark Office*